United States Patent
Pedrazzi

(10) Patent No.: US 6,730,233 B2
(45) Date of Patent: May 4, 2004

(54) DEVICE AND METHOD FOR CONTROLLING INFUSION OF LIQUID IN AN EXTRACORPOREAL BLOOD CIRCUIT

(75) Inventor: Renato Pedrazzi, Mirandola (IT)

(73) Assignee: Gambro Hospal (Schweiz) AG, Basel (SE)

( * ) Notice: Subject to any disclaimer, the term of this patent is extended or adjusted under 35 U.S.C. 154(b) by 90 days.

(21) Appl. No.: 09/980,864

(22) PCT Filed: Apr. 2, 2001

(86) PCT No.: PCT/IB01/00544

§ 371 (c)(1),
(2), (4) Date: Apr. 12, 2002

(87) PCT Pub. No.: WO01/76661

PCT Pub. Date: Oct. 18, 2001

(65) Prior Publication Data

US 2002/0121471 A1 Sep. 5, 2002

(30) Foreign Application Priority Data

Apr. 7, 2000 (IT) ..................... TO2000A0333

(51) Int. Cl.[7] ................. A61M 1/14; B01D 61/28; B01D 61/32; B01D 61/34

(52) U.S. Cl. .................. 210/739; 210/85; 210/90; 210/97; 210/109; 210/134; 210/143; 210/321.6; 210/321.65; 210/321.71; 210/645; 210/646; 210/650; 210/741; 604/4.01; 604/5.01; 604/6.09; 604/6.1; 604/6.11

(58) Field of Search ............... 210/85, 90, 97, 210/109, 134, 143, 321.6, 321.65, 321.71, 645, 646, 650, 739, 741, 745; 604/4.01, 5.01, 6.09, 6.1, 6.11

(56) References Cited

U.S. PATENT DOCUMENTS 5,762,805 A * 6/1998 Truitt et al. ............... 210/645
6,471,872 B2 * 10/2002 Kitaevich et al. ......... 210/739

FOREIGN PATENT DOCUMENTS

| DE | 4240681 A1 | 6/1994 |
| DE | 19654746 A1 | 7/1998 |
| EP | 1095666 A1 | 5/2001 |
| EP | 1 097 724 A2 | 5/2001 |
| WO | WO98/50091 | 11/1998 |
| WO | WO00/09182 | 2/2000 |

OTHER PUBLICATIONS

English translation copy of WO 98/50091 A1 published on Nov. 12, 1998.*
Bene, "Haemofiltration Machine for Indepentently Controlling the Concentration of at Least Two Ionic Substances in a Patient's Internal Medium", U.S. Patent Application Ser. No. 09/708,740, filed Nov. 6, 2000.

* cited by examiner

Primary Examiner—John Kim
(74) Attorney, Agent, or Firm—Finnegan, Henderson, Farabow, Garrett & Dunner LLP

(57) ABSTRACT

A dialysis machine includes an extracorporeal blood circuit having an arterial pipe and a venous pipe respectively connected to an inlet and an outlet of a blood compartment of a filter. The blood compartment and a dialysis liquid compartment of the filter are separated by a semi-permeable membrane. The machine is configured to determine a sequence of infusion of a liquid in the extracorporeal blood circuit, from at least one characteristic value correlated with the concentration of the blood and/or a filtration efficiency of the filter, and to infuse the infusion solution in the arterial pipe and in the venous pipe in accordance with the determined infusion sequence.

25 Claims, 2 Drawing Sheets

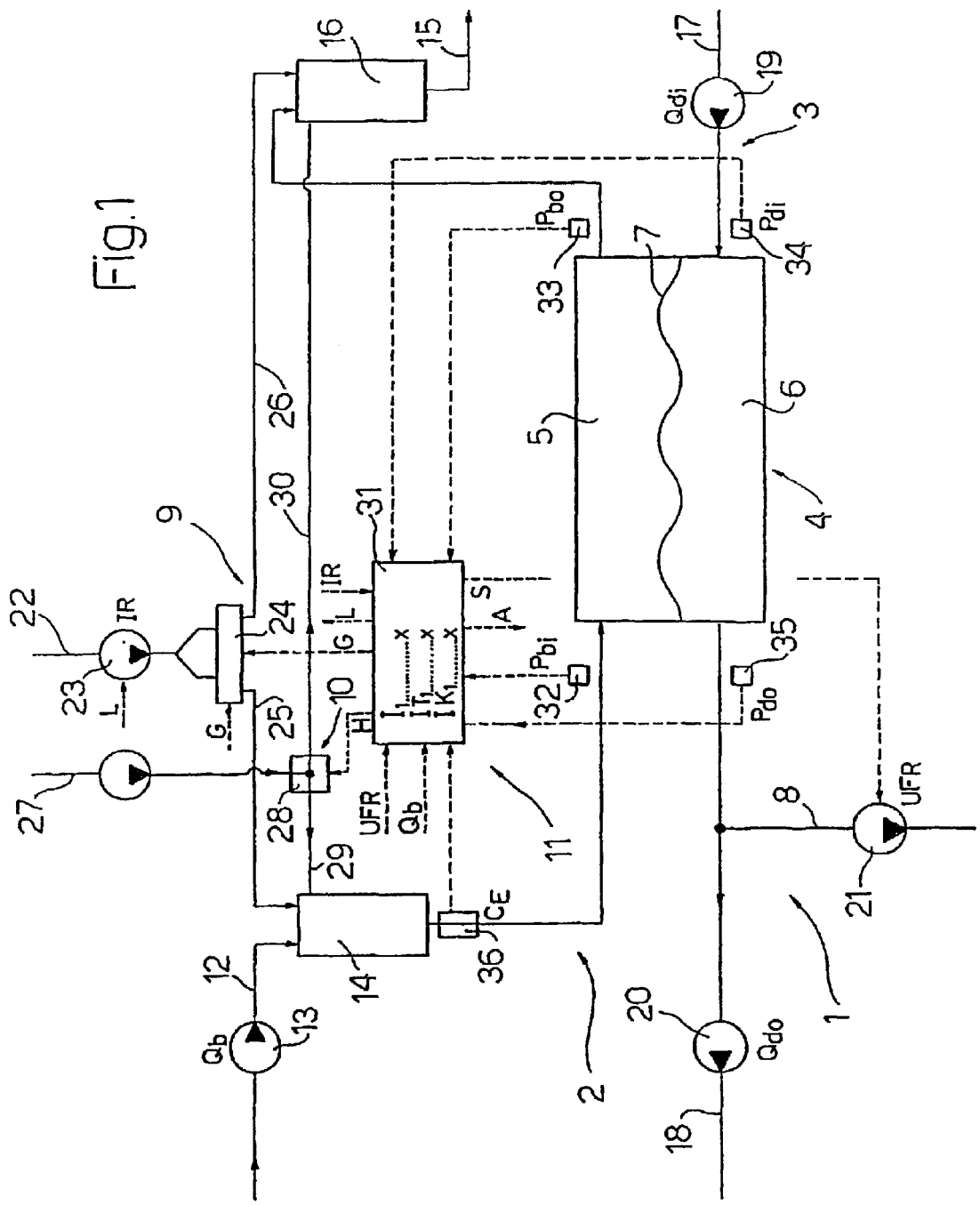

DEVICE AND METHOD FOR CONTROLLING INFUSION OF LIQUID IN AN EXTRACORPOREAL BLOOD CIRCUIT

CROSS REFERENCE TO RELATED APPLICATIONS

This application is a national phase application based on PCT/IB01/00544, filed Apr. 2, 2001, and claims the priority of Italian patent application no, TO2000A000333, filed Apr. 7, 2000.

BACKGROUND OF THE INVENTION

1. Field of the Invention

The present invention relates to a device and method for infusing a liquid in an extracorporeal blood circuit of a dialysis machine.

2. Description of the Related Art

As is well known, blood is composed of a liquid part called blood plasma and a corpuscular part formed by the blood cells, including, among others, the red blood cells. In cases of renal insufficiency, apart from the aforementioned components, the blood also contains metabolic waste (urea, creatinine) in excess which must be removed by means of a dialysis treatment effected by a dialysis machine.

A dialysis machine a generally comprises:
- a filter (dialyzer) comprising a blood compartment and a dialysis liquid compartment separated from one another by a semi-permeable membrane
- an extracorporeal blood circuit, which is connected to the blood compartment of the filter; and
- a dialysis liquid circuit, which is connected to the dialysis liquid compartment of the filter.

In use, the blood to be treated and a dialysis liquid respectively pass through these compartments, generally flowing in counter-current.

During dialysis treatment, there is migration of metabolic waste from the blood compartment to the dialysis liquid compartment through the semipermeable membrane by diffusion. Metabolic waste is also transferred by convection, from the blood compartment to the dialysis liquid compartment, when ultrafiltration of plasma water is caused through the membrane in order that the patient lose a determined weight during the treatment.

To increase the efficiency of dialysis treatment, it is also known to cause the ultrafiltration of large amounts of plasma water, so as to enhance the effects of transport of the undesirable waste by convection. The quantity of plasma water removed in excess relative to the desired final weight loss is compensated with a substitution liquid, which is infused into the extracorporeal blood circuit. The substitution liquid is infused either upstream from the filter (pre-dilution technique) or downstream from the filter (post-dilution technique). The infusion liquid generally consists of a solution with physiological composition and concentration.

Both pre-dilution and post-dilution techniques have their respective advantages and disadvantages.

In the post-dilution technique, the plasma water removed through the membrane is more concentrated than in the pre-dilution technique and, at equal flows, the treatment is more efficient. On the other hand, with the post-dilution technique, blood becomes more easily concentrated, which can slower the blood flow in the filter as well as the ultrafiltration of plasma water (through partial clogging of the filter itself), giving rise to the phenomenon called filter "caking". Consequently, the post-dilution technique permits extraction of a more limited quantity of plasma water than with the pre-dilution technique.

With the pre-dilution technique, the critical conditions leading to "caking" are avoided and the ultrafiltration efficiency is increased. However, at equal flows, the pre-dilution technique is less efficient than the post-dilution technique.

SUMMARY OF THE INVENTION

The aim of the present invention is to provide a device and a method for infusing a liquid into an extracorporeal blood circuit of a dialysis machine that do not have the drawbacks described above.

According to the present invention, a dialysis machine comprises:
- a filter having a blood compartment and a dialysis liquid compartment separated by a semi-permeable membrane;
- an extracorporeal blood circuit having an arterial pipe connected to an inlet of the blood compartment and a venous pipe connected to an outlet of the blood compartment;
- a dialysis liquid circuit having a supply pipe connected to an inlet of the dialysis liquid compartment and a drain pipe connected to an outlet of the dialysis liquid compartment;
- a infusion circuit having a pre-dilution pipe connected to the arterial pipe and a post-dilution pipe connected to the venous pipe;
- means for varying the flow of an infusion liquid in the pre-dilution pipe and in the post-dilution pipe, and
- control means for controlling the flow varying means so that the flow of the infusion liquid in the pre-dilution pipe and the post-dilution pipe matches a determined sequence.

The dialysis machine according to the invention may comprise one or more or the following features:
- the control means comprises means for determining the infusion sequence from at least one characteristic value (FF, $TMP_{ave}$, $K_{uf}$) correlated with the concentration of the blood ($C_E$) and/or the filtration efficiency of the filter.
- the control means comprises means for comparing the characteristic value (FF, $TMP_{ave}$, $K_{uf}$) with a series of intervals ($I_1 \ldots x, IT_1 \ldots x, IK_1 \ldots x$), each interval ($I_1 \ldots x\ IT_1 \ldots x, IK_1 \ldots X$) being associated with at least a predetermined control signal (S, G, H, L).
- the infusion varying means comprises a valve means for alternately occluding the pre-dilution pipe and the post-dilution pipe, and the predetermined control signal (G) defines a sequence for opening and closing the valve means.
- the infusion varying means comprises an infusion pump for circulating the infusion liquid, and the predetermined control signal (L) is for regulating the flow rate (IR) of liquid generated by the infusion pump.
- the dialysis machine comprises a ultrafiltration pump for causing ultrafiltration of plasma water through the membrane of the filter, and the predetermined control signal (S) is for regulating the flow rate (UFR) of liquid generated by the ultrafiltration pump.
- the dialysis machine comprises a bubble trap connected to the arterial pipe and a bubble trap connected to the venous pipe and means for injecting or withdrawing air into/from the bubble traps so as to adjust the level of liquid therein, and in the predetermined control signal (S) is for controlling the means for injecting or withdrawing air into/from the bubble traps.

the dialysis machine comprises:
  means for determining a ultrafiltration flow rate (UFR) of plasma water through the membrane of the filter;
  means for determining the haematocrit (Hct) at the inlet of the filter, and
  means for calculating the characteristic value as a filtration factor (FF) equal to $UFR/[Q_b(1-Hct)]$.

the dialysis machine comprises:
  means for measuring the blood pressure values ($P_{bo}$, $P_{bi}$) at the inlet and at the outlet of the blood compartment of the filter;
  means for measuring the dialysis liquid pressure values ($P_{di}$, $P_{do}$) at the inlet and at the outlet of the dialysis liquid compartment of the filter;
  means for calculating an inlet transmembrane pressure value ($TMP_i$) as the difference between the pressure value ($Pb_i$) at the inlet of the blood compartment and the pressure value ($Pd_o$) at the outlet of the dialysis liquid compartment and an outlet transmembrane pressure value ($TMP_o$) as the difference between the pressure value ($P_{bo}$) at the outlet of the blood compartment and the pressure value ($P_{di}$) at the inlet of the dialysis liquid compartment;
  means for calculating the characteristic value as a mean transmembrane pressure value ($TMP_{ave}$) equal to $[TMP_i-TMP_o]/2$.

the dialysis machine comprises:
  means for determining a ultrafiltration flow rate (UFR) of plasma water through the membrane of the filter;
  means for calculating the characteristic value as an actual permeability ($K_{uf}$) equal to the ratio between the ultrafiltration flow rate (UFR) and the mean transmembrane pressure value ($TMP_{ave}$).

Another object of the present invention is a method for infusing an infusion liquid into an extracorporeal blood circuit of a dialysis liquid machine, the extracorporeal blood circuit having an arterial pipe connected to an inlet of a blood compartment of a filter, and a venous pipe connected to an outlet of the blood compartment, the filter having a blood compartment and a dialysis liquid compartment separated by a semi-permeable membrane, characterized in that it comprises the steps of;
  determining an infusion sequence from at least one characteristic value (FF, $TMP_{ave}$, $K_{uf}$) correlated with the concentration of the blood ($C_E$) and/or a filtration efficiency of the filter, and
  infusing the infusion solution in either one or both of the arterial pipe and in the venous pipe in accordance with the determined infusion sequence.

BRIEF DESCRIPTION OF THE DRAWINGS

For better understanding of the present invention an embodiment thereof will now be described, referring to the appended drawings, in which:

FIG. 1 is a schematic representation of a dialysis machine;

DETAILED DESCRIPTION OF THE PREFERRED EMBODIMENT

Figure 3:
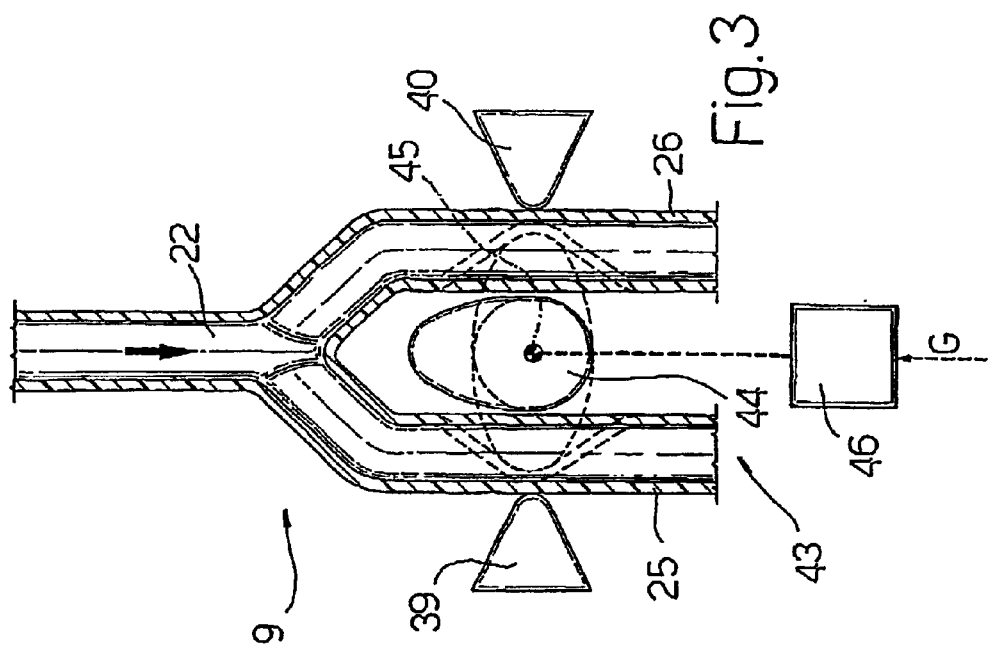
FIG. 3 is a schematic representation of a variant of the detail in FIG. 2.

In FIG. 1, a dialysis machine 1 comprises an extracorporeal blood circuit 2, a dialysis liquid circuit 3 and a filter 4 (dialyzer) having a blood compartment 5 and a dialysis liquid compartment 6 separated by a semi-permeable membrane 7.

The extracorporeal blood circuit 2 comprises an arterial pipe 12 and a venous pipe 15, respectively connected to an inlet and an outlet of the blood compartment 5 of the filter 4. The arterial pipe 12 is fitted with a peristaltic pump 13 supplying a blood flow $Q_b$ and a bubble trap 14, and the venous pipe 15 is fitted with a bubble trap 16.

The dialysis liquid circuit 3 comprises a supply pipe 17 and a drain pipe 18, respectively connected to an inlet and an outlet of the dialysis liquid compartment 6 of the filter 4. The supply pipe 17 is fitted with a pump 19 supplying a fresh dialysis liquid flow $Q_{di}$ and the drain pipe 18 is fitted with a pump 20 supplying a used liquid flow $Q_{do}$. In Use, the upstream end of the supply pipe 17 is connected to a source of fresh dialysis liquid (not shown).

A ultrafiltration pipe 8 is connected to the drain pipe 18 between the filter 4 and the pump 20 and is fitted with an ultrafiltration pump 21 supplying a flow UFR.

An infusion pipe 9 is connected to the extracorporeal blood circuit 2. It comprises a main pipe 22, which forks into a pre-dilution pipe 25 connected to the arterial bubble trap 14 and a post-dilution pipe 26 connected to the venous bubble trap 16. The main pipe 9 is fitted with an infusion pump 23 supplying a flow IR. A valve set 24 is arranged directly downstream from the fork on the pre-dilution and post-dilution pipes 25, 26. In use, the upstream end of the main pipe 22 is connected to a source of sterile solution (not shown).

A compressed air line 10 comprises a main pipe 27 which forks into two secondary pipes 29 and 30, respectively connected to the arterial and venous bubble traps 14, 15. A valve set 28 is arranged at the connection between the main and secondary air pipes.

The control circuit 11 comprises a control unit 31, a sensor 32 positioned on the arterial pipe 12 directly upstream from the filter 4 for supplying a signal $P_{bi}$ correlated to the blood pressure at the inlet of the filter 4, a sensor 33 positioned on the venous pipe 15 directly downstream from the filter 4 for supplying a signal $P_{bo}$ correlated to the blood pressure at the outlet of the filter 4, a sensor 34 positioned on the supply pipe 17 for supplying a signal $P_{di}$ correlated to the pressure of the dialysis liquid at the inlet of the filter 4, and a sensor 35 positioned on the drain pipe 18 for supplying a signal $P_{do}$ correlated to the pressure of the dialysis liquid at the outlet of the filter 4. The control circuit 11 also comprises a haemoconcentration sensor 36 arranged along pipe 12 between the filter 4 and the bubble trap 14 for producing a haemoconcentration signal $C_E$.

The signals $P_{bi}$, $P_{bo}$, $P_{di}$, $P_{do}$ and $C_E$ and the set values of various parameters, such as the blood flow rate $Q_b$, the flow rates ($Q_{di}$, $Q_{do}$) of the dialysis liquid in the supply pipe 17 and in the drain pipe 18, the ultrafiltration flow rate UFR, and the infusion flow rate IR are received by the central unit 31 for controlling the operation of the machine 1. In practice, the central unit 31 emits output signals for controlling the valve sets 24 and 28, the ultrafiltration pump 21 and the infusion pump 23, as will be made clear in the rest of the description.

Figure 2:
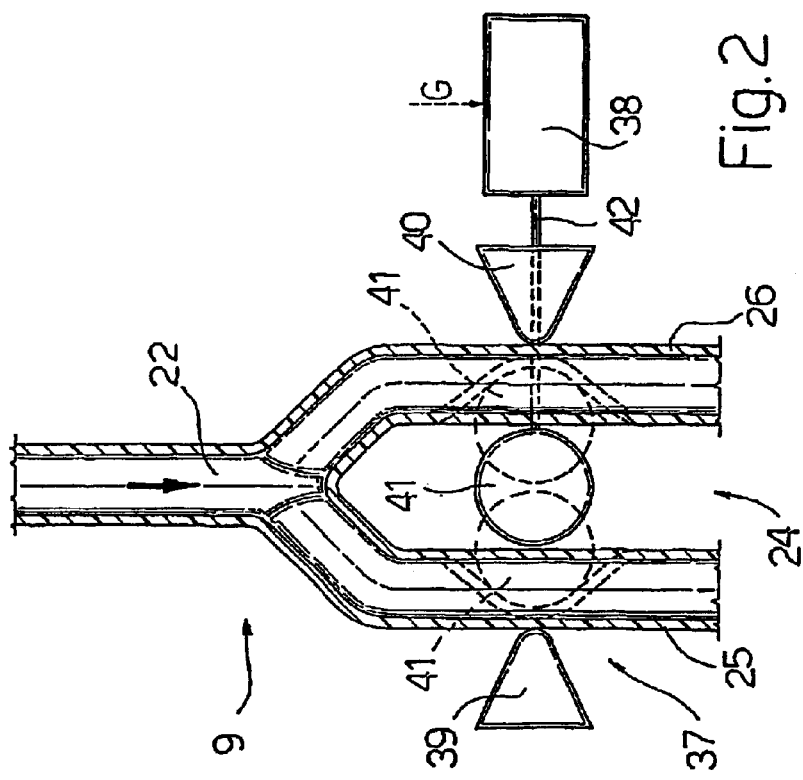
FIG. 2 is a schematic representation of a detail of the machine of FIG. 1.

Referring to FIG. 2, the valve set 24 comprises a double-pinch valve 37 and an electromagnet 38 for operating the valve 37. The valve 37 is positioned on the infusion pipes 25 and 26 in a position where the pipes 25 and 26 are substantially parallel, and comprises two fixed and opposite members 39 and 40, which are arranged in contact with the pipes 25 and 26 respectively, and a movable member 41, which is positioned between the pipes 25 and 26 and between the fixed members 39 and 40. The movable element 41 is connected to a slide 42 of the electromagnet 38 and can move between a position of rest, shown by a solid line in FIG. 2, and two operating positions, shown by dashed lines in FIG. 2.

According to the variant in FIG. 3, the valve set 24 comprises a pinch valve 43, which comprises a cam-type movable member 44, which can rotate about an axis 45 and is caused to rotate by an electric stepping motor 46. Cam-member 43 occupies two positions of rest about axis 45, one of which is shown by a solid line in FIG. 3, and two operating positions, shown by dashed lines in FIG. 3.

In use, the infusion of liquid is regulated by adjusting the delivery, by the pump 23, of a liquid (generally a solution possessing physiological composition and concentration) upstream and downstream from the filter 4.

The machine 1 operates on the basis of studies undertaken by the applicant, which demonstrated that the occurrence of some critical conditions does not depend on the absolute value of the individual quantities being monitored, but on the amount of liquid removed by ultrafiltration with respect to the plasma flow at the filter inlet.

Since the plasma flow depends on the blood flow $Q_b$, and on the initial concentration of the blood, according to one embodiment of the invention, the values of the blood flow $Q_b$, the ultrafiltration flow rate UFR and the concentration of the blood $C_E$ are acquired; the filtration factor FF, defined below, is determined on the basis of these quantities:

$$FF = UFR/Q_p = UFR/[Q_b(1-Hct)]$$

in which $Q_p$ is the plasma flow and Hct is the haematocrit which is related to the concentration of the blood $C_E$. The filtration factor is a quantity that is correlated with the concentration of the blood $C_E$. The control unit 31 compares the filtration factor FF determined using the above equation with a series of intervals $I_1 \ldots X$, which are each associated with corresponding values of the respective signals S, G, H, L and A at the output of control unit 31. When the filtration factor FF is within a defined interval $I_x$, the central control unit 31 ascribes defined values to the corresponding output signals G, H, S and L for operating, respectively, the valve sets 24 and 28 and/or the ultrafiltration pump 21, and the infusion pump 23.

This control situation is shown schematically in FIG. 1 by the control signals G, H, S and L generated by the control unit 31 and acting respectively on the valve sets 24 and 28 and on the ultrafiltration pump 21 and the infusion pump 23, and by a signal A supplied to a display unit (not shown).

The control of the operating point of filter 4 also permits its optimization. In practice, for each interval $I_1 \ldots x$, there is a corresponding particular operating condition of the machine 1; specifically each particular operating condition can comprise, in combination, a particular distribution of the infusion liquid in pre-dilution and in post-dilution by acting upon valve set 24, a variation of the ultrafiltration flow rate UFR by acting on the pump 21 and a variation of the infusion flow rate IR by acting on the pump 23. By adjusting the valve set 28 it is possible to change the amount of air inside the bubble traps 14 and 16 when there is a variation of the pre-dilution and post-dilution flow rates.

The concentration of the blood $C_E$ can be measured directly, via the haematocrit Hct, or indirectly by measuring the haemoglobin (in which case the value of the haematocrit Hct is obtained by dividing the measured haemoglobin value Hgb by the cellular mean concentration of the haemoglobin (Hcmc) or by measurements of the viscosity, the electrical conductivity or the density of the blood, in a known manner which will not be described in detail).

The signals S and L are for controlling the motors of the pumps 21 and 23 so as to increase or decrease the flow rates UFR and IR.

The signal H is for controlling the valve set 28 and for determining the amount of air in the bubble traps 14 and 16 in relation to the pre-dilution and post-dilution flow rates.

Referring to FIG. 2, the signal G is a control signal for exciting the electromagnet 38 according to a predetermined sequence. In other words, the distribution of the infusion flow in the two pipes 25, 26 results from the alternate opening and closing of the pre-dilution and post-dilution pipes 25 and 26 by means of the movable member 41 operated by electromagnet 38 according to a sequence defined by signal G.

The control sequences comprise, in addition to the combined operating mode between pre-dilution and post-dilution, the exclusive pre-dilution operating mode and the exclusive post-dilution operating mode. The movable member 41 is displaced alternately against the fixed members 39 and 40 so as to pinch the infusion pipes 25 and 26 alternately and so as to interrupt the infusion flow in pipes 25 and 26 cyclically and according to a defined sequence.

The valve set 24 in FIG. 3 operates like the valve set in FIG. 2, so as to cause the alternation of the closed position of the pipes 25 and 26. In this case, the signal G defines a particular sequence of the angular position of the motor 46 which determines, in turn, the position of the movable member 44.

According to one variant of the invention, the pre-dilution and post-dilution positions together with the ultrafiltration flow rate UFR and the infusion flow rate IR are adjusted in relation to the mean transmembrane values:

$$TMP_{ave} = [TMP_i - TMP_o]/2$$

calculated from the four pressures measured at the inlet and outlet of the blood compartment 5 and of the dialysis liquid compartment 6 of the filter 4, (in this formula, $TMP_i$ is the transmembrane pressure value, which is equal to the difference between the pressure value ($P_{bi}$) at the inlet of the blood compartment (5) and the pressure value ($P_{do}$) at the outlet of the dialysis liquid compartment (6), and $TMP_o$ is the outlet transmembrane pressure value, which is equal to the difference between the pressure value ($Pb_o$) at the outlet of the blood compartment (5) and the pressure value ($Pd_i$) at the inlet of the dialysis liquid compartment (6)).

Here also, the mean transmembrane values are compared with respective intervals $IT_1 \ldots x$, which are each associated with corresponding respective signals G, H, S and L for operating the valve sets 24 and 28, the ultrafiltration pump 21 and the infusion pump 23.

According to another variant, pre-dilution and post-dilution positions together with the flow rates of ultrafiltration UFR and infusion IR are regulated in relation to the actual permeability values of the membrane, defined as:

$$K_{uf} = UFR/TMP_{ave}$$

The values of the actual permeability $K_{uf}$ are compared with respective intervals $IK_1 \ldots x$, which are each associated with corresponding respective signals G, H, L and S for operating the valve sets 24 and 28, the ultrafiltration pump 21 and the infusion pump 23.

The techniques for determining the operating conditions of the filter 4 and the state of the membrane 7 can be applied individually as described above or in combination as described in the applicant's patent application TO99000680 filed on Jul. 30, 1999.

The method based on the filtration factor FF can be employed in combination either with the method based on the mean transmembrane values $TMP_{ave}$, or with the method based on the permeability values $K_{uf}$.

The advantages of the present method are clear from the above description. It is emphasized, in particular, that the present method permits accurate regulation and distribution of the infusion flow rate IR. Moreover, since the present method is based on the monitoring of quantities that are directly correlated with the operating conditions of the filter 4, it immediately supplies the magnitude of the changes required, or at any rate greatly simplifies the determination of these changes, for the purpose of improving the filtration efficiency and avoiding critical situations. Furthermore, the present method does not require modification of the dialysis machine, since the control unit 31 can be implemented with the unit, already provided, for controlling the dialysis treatment, and the quantities employed are already available or can easily be obtained by mathematical methods from the measured or imposed quantities.

What is claimed is:

1. A dialysis machine comprising:
    a filter having a blood compartment and a dialysis liquid compartment separated by a semi-permeable membrane;
    an extracorporeal blood circuit having an arterial pipe connected to an inlet of the blood compartment and a venous pipe connected to an outlet of the blood compartment;
    a dialysis liquid circuit having a supply pipe connected to an inlet of the dialysis liquid compartment and a drain pipe connected to an outlet of the dialysis liquid compartment;
    an infusion circuit having a pre-dilution pipe connected to the arterial pipe and a post-dilution pipe connected to the venous pipe;
    means for varying the flow of an infusion liquid in the pre-dilution pipe and in the post-dilution pipe, and
    control means for controlling the flow varying means so that the flow of the infusion liquid in the pre-dilution pipe and the post-dilution pipe matches a determined sequence,
    wherein the control means comprises means for determining the infusion sequence from at least one characteristic value correlated with concentration of the blood ($C_E$) and/or filtration efficiency of the filter, said at least one characteristic value being selected from at least one of filtration factor (FF), mean transmembrane pressure ($TMP_{ave}$), and actual permeability of the membrane ($K_{uf}$).

2. The dialysis machine according to claim 1, wherein the control means comprises means for comparing said at least one characteristic value with a series of intervals ($I_{1...x}$, $IT_{1...x}$, $IK_{1...x}$), each interval ($I_{1...x}$, $IT_{1...x}$, $IK_{1...x}$) being associated with at least a predetermined control signal (S, G, H, L).

3. The dialysis machine according to claim 2, wherein the infusion varying means comprises a valve means for alternately occluding the pre-dilution pipe and the post-dilution pipe, and in that the predetermined control signal (G) defines a sequence for opening and closing the valve means.

4. The dialysis machine according to claim 2, wherein the infusion varying means comprises an infusion pump for circulating the infusion liquid, and in that the predetermined control signal (L) is for regulating the flow rate (IR) of liquid generated by the infusion pump.

5. The dialysis machine according to claim 2, further comprising an ultrafiltration pump for causing ultrafiltration of plasma water through the membrane of the filter, and wherein the predetermined control signal (S) is for regulating the flow rate (UFR) of liquid generated by the ultrafiltration pump.

6. A dialysis machine according to claim 2, further comprising a bubble trap connected to the arterial pipe and a bubble trap connected to the venous pipe and means for injecting or withdrawing air into/from the bubble traps so as to adjust the level of liquid therein, and wherein the predetermined control signal (S) is for controlling the means for injecting or withdrawing air into/from the bubble traps.

7. A dialysis machine according to claim 1, further comprising:
    means for determining an ultrafiltration flow rate (UFR) of plasma water through the membrane of the filter;
    means for determining the haematocrit (Hct) at the inlet of the filter, and
    means for calculating the characteristic value as a filtration factor (FF) equal to $UFR/[Q_b(1-Hct)]$, where Q is blood flow rate.

8. A dialysis machine according to claim 7, wherein the means for determining the haematocrit (Hct) comprises means for determining the haemoglobin concentration at the inlet of the filter and means for dividing the haemoglobin concentration by a constant coefficient.

9. A dialysis machine according to claim 1, further comprising:
    means for measuring the blood pressure values ($P_{bi}$, $P_{bo}$) at the inlet and at the outlet of the blood compartment of the filter;
    means for measuring the dialysis liquid pressure values ($P_{di}$, $P_{do}$) at the inlet and at the outlet of the dialysis liquid compartment of the filter;
    means for calculating an inlet transmembrane pressure value ($TMP_i$) as the difference between the pressure value ($P_{bi}$) at the inlet of the blood compartment and the pressure value ($P_{do}$) at the outlet of the dialysis liquid compartment and an outlet transmembrane pressure value ($TMP_o$) as the difference between the pressure value ($P_{bo}$) at the outlet of the blood compartment and the pressure value ($P_{di}$) at the inlet of the dialysis liquid compartment; and
    means for calculating the characteristic value as a mean transmembrane pressure value ($TMP_{ave}$) equal to $[TMP_i-TMP_o]/2$.

10. A dialysis machine according to claim 9, further comprising:
    means for determining an ultrafiltration flow rate (UFR) of plasma water through the membrane of the filter; and
    means for calculating the characteristic value as an actual permeability ($K_{uf}$) equal to the ratio between the ultrafiltration flow rate (UFR) and the mean transmembrane pressure value ($TMP_{ave}$).

11. A dialysis machine comprising:
    a filter having a blood compartment and a dialysis liquid compartment separated by a semi-permeable membrane;
    an extracorporeal blood circuit having an arterial pipe connected to an inlet of the blood compartment and a venous pipe connected to an outlet of the blood compartment;

a dialysis liquid circuit having a supply pipe connected to an inlet of the dialysis liquid compartment and a drain pipe connected to an outlet of the dialysis liquid compartment;

an infusion circuit having a main pipe which forks into a pre-dilution pipe connected to the arterial pipe and a post-dilution pipe connected to the venous pipe;

a valve set arranged downstream from the fork on the pre-dilution and post-dilution pipes;

an infusion pump on the main pipe supplying a flow IR; and a control unit operating the infusion pump, for causing a variation of the infusion flow rate, and acting upon the valve set, for causing a particular distribution of the flow of the infusion liquid in the pre-dilution pipe and the post-dilution pipe, the flow of the infusion liquid in the pre-dilution pipe and the post-dilution pipe being caused to match a determined infusion sequence determined from at least one characteristic value correlated with a concentration of the blood ($C_E$) and/or a filtration efficiency of the filter, said at least one characteristic value being selected from at least one of filtration factor (FF), mean transmembrane pressure ($TMP_{ave}$), and actual permeability of the membrane ($K_{uf}$).

12. A dialysis machine comprising:

a filter having a blood compartment and a dialysis liquid compartment separated by a semi-permeable membrane;

an extracorporeal blood circuit having an arterial pipe connected to an inlet of the blood compartment and a venous pipe connected to an outlet of the blood compartment;

a dialysis liquid circuit having a supply pipe connected to an inlet of the dialysis liquid compartment and a drain pipe connected to an outlet of the dialysis liquid compartment;

an infusion circuit having a main pipe which forks into a pre-dilution pipe connected to the arterial pipe and a post-dilution pipe connected to the venous pipe;

a valve set arranged downstream from the fork on the pre-dilution and post-dilution pipes;

an infusion pump on the main pipe supplying a flow IR;

a bubble trap connected to the arterial pipe and a bubble trap connected to the venous pipe;

a compressed air line comprising a main pipe which forks into two secondary pipes and, respectively connected to the arterial and venous bubble traps;

a valve set arranged at the connection between the main and secondary air pipes; and a control unit determining at least one characteristic value correlated with a concentration of the blood ($C_E$) and/or a filtration efficiency of the filter, said at least one characteristic value being selected from at least one of filtration factor (FF), mean transmembrane pressure ($TMP_{ave}$), and actual permeability of the membrane ($K_{uf}$), comparing said at least one characteristic value with a series of intervals ($I_{1\ldots x}$, $IT_{1\ldots x}$, $IK_{1\ldots x}$), each interval ($I_{1\ldots x}$, $IT_{1\ldots x}$, $IK_{1\ldots x}$) being associated with corresponding values of respective control signals (S, G, H, L), ascribing defined values to the corresponding output signals (G, H, S and L) for operating, respectively, the valve sets, the ultrafiltration pump, and the infusion pump, operating the infusion pump with output signal (L), for causing a variation of the infusion flow rate, acting upon the valve set with output signal (G), for causing a particular distribution of the flow of the infusion liquid in the pre-dilution pipe and the post-dilution pipe, acting on pump with output signal (S), for causing a variation of ultrafiltration flow rate UFR, and adjusting the valve set with output signal (H) to change an amount of air inside the bubble traps.

13. A dialysis machine according to claim 12, comprising:

a haemoconcentration sensor at the inlet of the filter for producing a haemoconcentration signal CE, the control unit calculating haematocrit (Hct) at the inlet of the filter and the characteristic value as a filtration factor (FF) equal to $UFR/[Q_b(1-Hct)]$, where UFR is a set ultrafiltration flow rate of plasma water through the membrane of the filter, and $Q_b$ is blood flow rate.

14. A dialysis machine according to claim 12, comprising:

sensors for measuring the blood pressure values ($P_{bi}$, $P_{bo}$) at the inlet and at the outlet of the blood compartment of the filter; and sensors for measuring the dialysis liquid pressure values ($P_{di}$, $P_{do}$) at the inlet and at the outlet of the dialysis liquid compartment of the filter;

the control unit calculating an inlet transmembrane pressure value ($TMP_i$) as the difference between the pressure value ($P_{bi}$) at the inlet of the blood compartment and the pressure value ($P_{do}$) at the outlet of the dialysis liquid compartment and an outlet transmembrane pressure value ($TMP_o$) as the difference between the pressure value ($P_{bo}$) at the outlet of the blood compartment and the pressure value ($P_{di}$) at the inlet of the dialysis liquid compartment; and the control unit calculating the characteristic value as a mean transmembrane pressure value ($TMP_{ave}$) equal to $[TMP_i-TMP_o]/2$.

15. A dialysis machine according to claim 12, wherein the control unit calculates the characteristic value as an actual permeability ($K_{uf}$) equal to the ratio between the set ultrafiltration flow rate (UFR) and the mean transmembrane pressure value ($TMP_{ave}$).

16. A method for infusing an infusion liquid in an extracorporeal blood circuit of a dialysis liquid machine, the extracorporeal blood circuit having an arterial pipe connected to an inlet of a blood compartment of a filter, and a venous pipe connected to an outlet of the blood compartment, the filter having a blood compartment and a dialysis liquid compartment separated by a semi-permeable membrane, comprising the steps of:

determining an infusion sequence from at least one characteristic value correlated with the concentration of the blood ($C_E$) and/or a filtration efficiency of the filter, said at least one characteristic value being selected from at least one of filtration factor (FF), mean transmembrane pressure ($TMP_{ave}$), and actual permeability of the membrane ($K_{uf}$), and infusing the infusion solution in either one or both of the arterial pipe and the venous pipe in accordance with the determined infusion sequence.

17. A method according to claim 16, further comprising the step of comparing said at least one characteristic value with a series of intervals ($I_{1\ldots x}$, $IT_{1\ldots x}$, $IK_{1\ldots x}$), each interval ($I_{1\ldots x}$, $IT_{1\ldots x}$, $IK_{1\ldots x}$) being associated with at least a predetermined control signal (S, G, H, L).

18. A method according to claim 17, wherein the predetermined control signal (G) defines a sequence for opening and closing a valve means arranged for alternately occluding a pre-dilution infusion pipe connected to the arterial line and a post-dilution infusion pipe connected to the venous line.

19. A method according to claim 17, wherein the predetermined control signal (L) is for regulating the flow rate (IR) of liquid generated by an infusion pump for circulating the infusion liquid.

20. A method according to claim 14, wherein the predetermined control signal (S) is for regulating the flow rate (UFR) of liquid generated by a ultrafiltration pump for causing ultrafiltration of plasma water through the membrane of the filter.

21. A method according to claim 17, wherein the predetermined control signal (S) is for controlling means for injecting or withdrawing air into/from bubble traps respectively connected to the arterial pipe and to the venous pipe.

22. A method according to claim 16, further comprising the steps of:
   determining a ultrafiltration flow rate (UFR) of plasma water through the membrane of the filter;
   determining the haematocrit (Hct) at the inlet of the filter, and
   calculating the characteristic value as a filtration factor (FF) equal to $UFR/[Q_b(1-Hct)]$, where $Q_b$ is blood flow rate.

23. A method according to claim 22, wherein the step of determining the haematocrit (Hct) comprises the step of determining the haemoglobin concentration at the inlet of the filter and the step of dividing the haemoglobin concentration by a constant coefficient.

24. A method according to claim 16, further comprising the steps of:
   measuring the blood pressure values ($P_{bi}$, $P_{bo}$) at the inlet and at the outlet of the blood compartment of the filter;
   measuring the dialysis liquid pressure values ($P_{di}$, $P_{do}$) at the inlet and at the outlet of the dialysis liquid compartment of the filter;
   calculating an inlet transmembrane pressure value ($TMP_i$) as the difference between the pressure value ($P_{bi}$) at the inlet of the blood compartment and the pressure value ($P_{do}$) at the outlet of the dialysis liquid compartment and an outlet transmembrane pressure value ($TMP_o$) as the difference between the pressure value ($P_{bo}$) at the outlet of the blood compartment and the pressure value ($P_{di}$) at the inlet of the dialysis liquid compartment; and
   calculating the characteristic value as a mean transmembrane pressure value ($TMP_{ave}$) equal to $[TMP_i-TMP_o]/2$.

25. A method according to claim 24, further comprising the steps of:
   determining a ultrafiltration flow rate (UFR) of plasma water through the membrane of the filter; and
   calculating the characteristic value as an actual permeability ($K_{uf}$) equal to the ratio between the ultrafiltration flow rate (UFR) and the mean transmembrane pressure value ($TMP_{ave}$).

* * * * *

UNITED STATES PATENT AND TRADEMARK OFFICE
CERTIFICATE OF CORRECTION

PATENT NO. : 6,730,233 B2
DATED : May 4, 2004
INVENTOR(S) : Renato Pedrazzi

It is certified that error appears in the above-identified patent and that said Letters Patent is hereby corrected as shown below:

Title page,
Item [73], Assignee, "(SE)" should read -- (CH) --.

Column 7,
Line 58, "$\mathbf{IK_{1...x}}$)being" should read -- $\mathbf{IK_{1...x}}$) being --.

Column 11,
Line 10, "claim 14," should read -- claim 17, --.
Line 21, "a ultrafiltration" should read -- an ultrafiltration --.

Column 12,
Line 23, "a ultrafiltration" should read -- an ultrafiltration --.

Signed and Sealed this

Thirtieth Day of November, 2004

JON W. DUDAS
*Director of the United States Patent and Trademark Office*